(12) United States Patent
Suzuki et al.

(10) Patent No.: US 11,779,877 B2
(45) Date of Patent: Oct. 10, 2023

(54) METHOD FOR REMOVING HALOGEN FLUORIDE, QUANTITATIVE ANALYSIS METHOD FOR GAS COMPONENT CONTAINED IN HALOGEN FLUORIDE MIXED GAS, AND QUANTITATIVE ANALYZER

(71) Applicant: SHOWA DENKO K.K., Tokyo (JP)

(72) Inventors: Atsushi Suzuki, Tokyo (JP); Kazuma Matsui, Tokyo (JP)

(73) Assignee: Resonac Corporation, Tokyo (JP)

( * ) Notice: Subject to any disclaimer, the term of this patent is extended or adjusted under 35 U.S.C. 154(b) by 142 days.

(21) Appl. No.: 17/416,807

(22) PCT Filed: Dec. 9, 2019

(86) PCT No.: PCT/JP2019/048055
§ 371 (c)(1),
(2) Date: Jun. 21, 2021

(87) PCT Pub. No.: WO2020/129726
PCT Pub. Date: Jun. 25, 2020

(65) Prior Publication Data
US 2022/0054972 A1 Feb. 24, 2022

(30) Foreign Application Priority Data

Dec. 21, 2018 (JP) .................. 2018-239516
Oct. 25, 2019 (JP) .................. 2019-194301

(51) Int. Cl.
*B01D 53/14* (2006.01)
*B01D 53/30* (2006.01)
(Continued)

(52) U.S. Cl.
CPC ..... *B01D 53/1456* (2013.01); *B01D 53/1493* (2013.01); *B01D 53/30* (2013.01);
(Continued)

(58) Field of Classification Search
CPC ............ B01D 53/1456; B01D 53/1493; B01D 53/30; B01D 53/685; B01D 53/04;
(Continued)

(56) References Cited

U.S. PATENT DOCUMENTS 2,732,410 A 1/1956 Farlow et al.
6,309,618 B1 10/2001 Ohira et al.
(Continued)

FOREIGN PATENT DOCUMENTS

JP H4-9757 A 1/1992
JP H07-97106 B2 10/1995
(Continued)

OTHER PUBLICATIONS

JP2007057371A English translation (Year: 2007).*
(Continued)

*Primary Examiner* — Anita Nassiri-Motlagh
(74) *Attorney, Agent, or Firm* — Sughrue Mion, PLLC

(57) ABSTRACT

A method for removing a halogen fluoride in a mixed gas by reacting the mixed gas containing a halogen fluoride including bromine or iodine with a removing agent, wherein the removing agent is a chloride, bromide or iodide of potassium, sodium, magnesium, calcium and barium. Also disclosed is a quantitative analysis method as well as a quantitative analyzer for a gas component contained in a hydrogen fluoride mixed gas, the method characterized by reacting a mixed gas containing a halogen fluoride and another gas component with a removing agent, thereby removing the halogen fluoride in the mixed gas, further removing produced by-products, and quantitatively analyzing a residual gas by a gas chromatograph.

8 Claims, 3 Drawing Sheets

(51) Int. Cl.
    *B01D 53/68*     (2006.01)
    *B01D 53/04*     (2006.01)

(52) U.S. Cl.
    CPC ............ *B01D 53/685* (2013.01); *B01D 53/04* (2013.01); *B01D 2251/108* (2013.01); *B01D 2251/304* (2013.01); *B01D 2251/306* (2013.01); *B01D 2251/404* (2013.01); *B01D 2251/408* (2013.01); *B01D 2252/10* (2013.01); *B01D 2257/2022* (2013.01); *B01D 2257/2027* (2013.01); *B01D 2257/2047* (2013.01)

(58) Field of Classification Search
    CPC ........ B01D 2251/108; B01D 2251/304; B01D 2251/306; B01D 2251/404; B01D 2251/408; B01D 2252/10; B01D 2257/2022; B01D 2257/2027; B01D 2257/2047
    USPC ......................................................... 423/210
    See application file for complete search history.

(56) References Cited

U.S. PATENT DOCUMENTS

| 10,926,211 | B2 | 2/2021 | Yao et al. |
| 2019/0046917 | A1 | 2/2019 | Yao et al. |

FOREIGN PATENT DOCUMENTS

| JP | 8-215539 | A | 8/1996 |
| JP | H8-215538 | A | 8/1996 |
| JP | 2725876 | B2 | 3/1998 |
| JP | 2000-157837 | A | 6/2000 |
| JP | 2000-254438 | A | 9/2000 |
| JP | 2007-057371 | A | 3/2007 |
| JP | 4642602 | B2 | 3/2011 |
| JP | 2012-106200 | A | 6/2012 |
| JP | 2017-141150 | A | 8/2017 |
| TW | 523491 | B | 3/2003 |
| TW | 201731763 | A | 9/2017 |
| WO | 2010/090118 | A1 | 8/2010 |

OTHER PUBLICATIONS

JP2017141150A English translation (Year: 2017).*
International Search Report dated Mar. 10, 2020 from the International Searching Authority in International Application No. PCT/JP2019/048055.
Written Opinion dated Mar. 10, 2020 from the International Searching Authority in International Application No. PCT/JP2019/048055.
Office Action dated Dec. 2, 2020 from the Taiwanese Intellectual Property Office in TW patent application No. 108145942.
"Chemistry and Technology of Uranium Fluoride", edited by the Editorial Board of the Nuclear Science Committee of the Chinese Academy of Sciences, 1965, Chinese Industry Press, p. 268 (4 pages total).
"Inorganic Chemistry vol. 1 (Second Edition)", edited by the Inorganic Chemistry Teaching and Research Sections of Beijing Normal University, Huazhong Normal University, and Nanjing Normal University, 1986, Higher Education Press, p. 408 (3 pages total).

* cited by examiner

[Fig. 1]
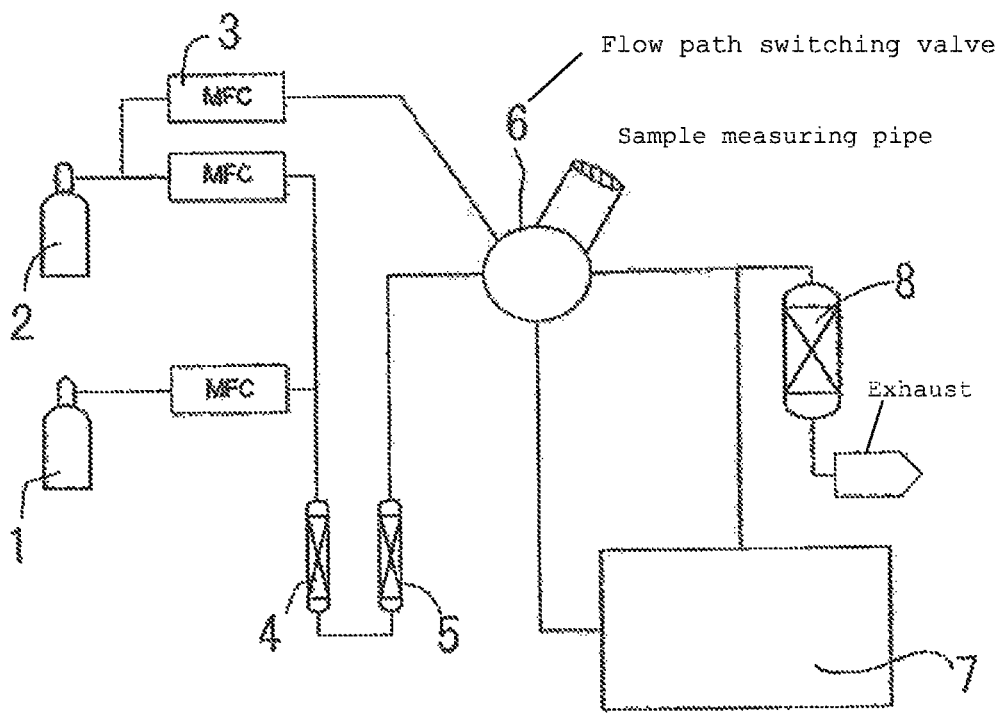

[Fig. 2]
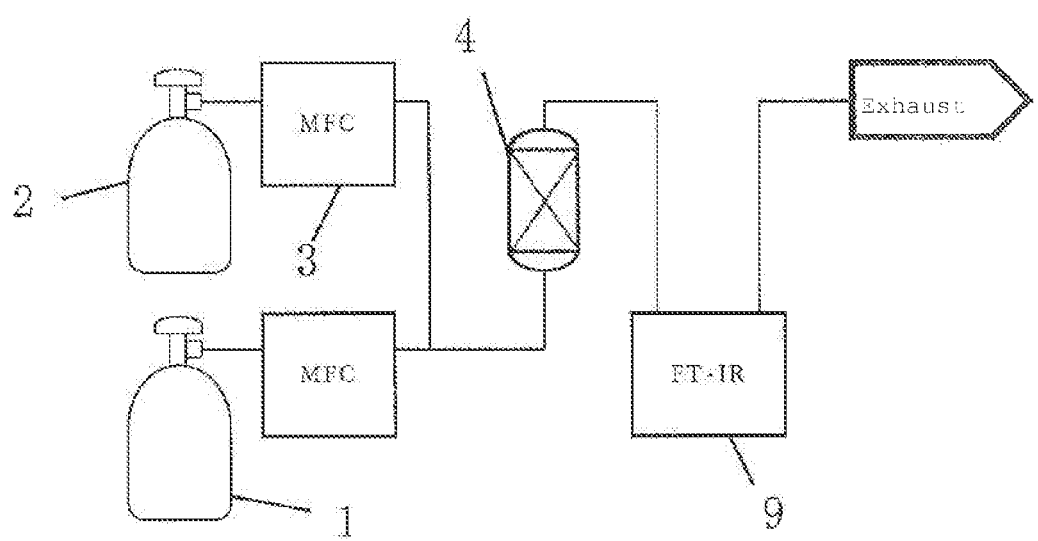

[Fig. 3]
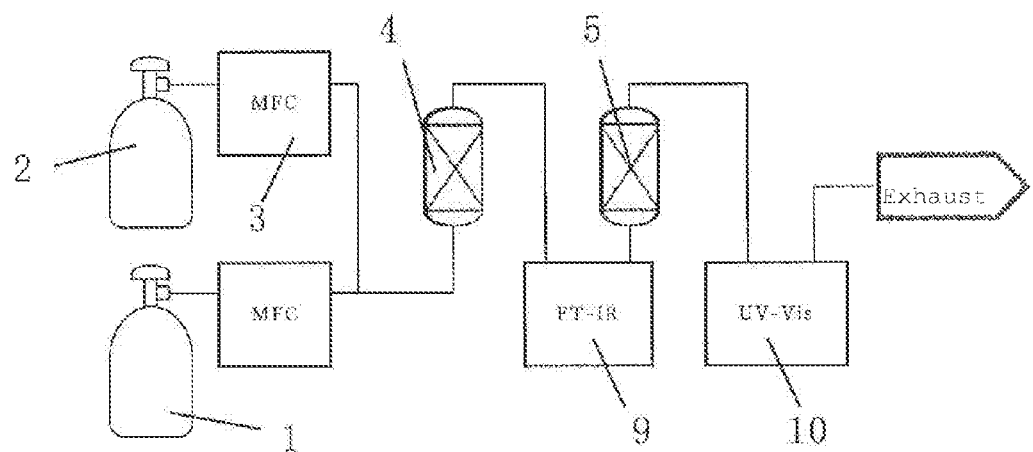

METHOD FOR REMOVING HALOGEN FLUORIDE, QUANTITATIVE ANALYSIS METHOD FOR GAS COMPONENT CONTAINED IN HALOGEN FLUORIDE MIXED GAS, AND QUANTITATIVE ANALYZER

CROSS REFERENCE TO RELATED APPLICATIONS

This application is a National Stage of International Application No. PCT/JP2019/048055 filed Dec. 9, 2019, claiming priority based on Japanese Patent Application Nos. 2018-239516 filed Dec. 21, 2018 and 2019-194301 filed Oct. 25, 2019.

TECHNICAL FIELD

The present invention relates to a method for removing a halogen fluoride containing bromine or iodine contained in a mixed gas.

The present invention also relates to a quantitative analysis method and a quantitative analyzer for trace impurity components accompanying a halogen fluoride containing bromine or iodine used as a semiconductor processing treatment gas. In more detail, the present invention relates to a method and an apparatus for quantitatively analyzing, simply and precisely, the impurity components such as oxygen, nitrogen, carbon dioxide and tetrafluoromethane contained in the mixed gas containing the halogen fluoride and another gas component.

BACKGROUND ART

A fluoride gas of a halogen other than a fluorine, namely, a halogen fluoride gas has been used in various applications such as for an excimer laser, for cleaning of a CVD apparatus, and as a gas for semiconductor processing treatment such as etching gas, and in conjunction with recent developments in the electronic industry, the application has expanded year-on-year.

Recently, as miniaturization of semiconductors has progressed, a high-purity gas has been demanded as an etching gas and a cleaning gas, and therefore an analysis method for precisely quantifying the trace impurities is required.

As a quantitative analysis method for impurities in for example a fluorine-based gas, Patent Literature 1 discloses a method for making a gas containing impurities in $F_2$, ClF, $ClF_3$, and $ClF_5$ pass through a chloride filling layer, converting the gas into a chloride gas, and then completely removing the chloride gas to analyze the trace impurities by a gas chromatograph. In Patent Literature 1, a sodium chloride is used as a chloride.

Further, Patent Literature 2 discloses a method for reacting a fluorine gas containing another gas component with a bromide to remove the produced bromine, and then quantitatively analyzing the residual gas having had the bromine removed therefrom, by a gas chromatograph.

Further, Patent Literature 3 discloses a method for reacting a gas containing a fluorine with an alkali compound such as $Ca(OH)_2$ to generate an oxygen gas, and then quantifying a fluorine gas component by quantifying the oxygen gas.

Further, in many cases, the halogen fluoride gases have high reactivity, high risk and high toxicity. For this reason, the halogen fluoride gas cannot be emitted as-is into the atmosphere.

Patent Literature 4 describes a method for removing a halogen-based gas by reacting the halogen-based gases such as $ClF_3$, $BrF_3$ and $BrF_5$ with a mixture of calcium hydroxide and potassium hydroxide, thereby solidifying the halogen-based gas as a solid halide.

CITATION LIST

Patent Literature

[Patent Literature 1] JP 2725876 B
[Patent Literature 2] JP 4642602 B
[Patent Literature 3] JP 7-97106 B2
[Patent Literature 4] JP 8-215538 A

SUMMARY OF INVENTION

Technical Problem

According to the method in Patent Literature 4, a solid alkali dissolves or deliquesces due to water produced by reaction of a halogen fluoride with calcium hydroxide, so that slurry is produced, and therefore it has been possible that the slurry sometimes blocks the tubes through which substances move.

The object of the present invention is to provide a method for removing which facilitates handling of an exhaust gas, by removing a halogen fluoride containing bromine or iodine in a state in which the possibility of such blocking is reduced.

The further object of the present invention is to provide a quantitative analysis method and a quantitative analyzer for trace impurities accompanying halogen fluorides such as a bromine fluoride and an iodine fluoride.

Solution to Problem

Under these circumstances, as a result of an earnest examination for achieving the above object, the present inventors have found out that removing halogen fluorides by reacting, with a removing agent, a mixed gas containing halogen fluorides and another gas component such as trace impurities, further removing produced by-products, and quantitatively analyzing the residual gas, so that the trace impurities accompanying the halogen fluorides can be quantified, thus completing the present invention. The constitution of the present invention is as follows.

[1] A method for removing a halogen fluoride in a mixed gas, characterized by reacting a mixed gas containing halogen fluoride including bromine or iodine and another gas component with a removing agent such as a chloride, bromide or iodide of an element selected from the group consisting of potassium, sodium, magnesium, calcium and barium.

[2] The method for removing a halogen fluoride according to [1], wherein a reaction temperature with the removing agent is 10° C. or higher and lower than 300° C.

[3] The method for removing a halogen fluoride according to [1], wherein the halogen fluoride is at least one selected from $BrF$, $BrF_3$, $BrF_5$, $IF_3$, $IF_5$ and $IF_7$.

[4] The method for removing a halogen fluoride according to [1] to [3], wherein the removing agent is a chloride of an element selected from the group consisting of potassium, sodium, magnesium, calcium and barium and a reaction temperature of the mixed gas with the chloride is 10° C. or higher and lower than 100° C.

[5] The method for removing a halogen fluoride according to [1] to [3], wherein the removing agent is a bromide or iodide of an element selected from the group consisting of potassium, sodium, magnesium, calcium and barium and a reaction temperature of the mixed gas and the bromide or iodide is 100° C. or higher and lower than 300° C.

[6] The method for removing a halogen fluoride according to [1], wherein another gas component contains at least one selected from oxygen, nitrogen, carbon dioxide, helium, argon, tetrafluoromethane, silicon tetrafluoride, sulfur hexafluoride, tungsten hexafluoride and chromium pentafluoride.

[7] The method for removing a halogen fluoride according to [1], wherein a reaction product is caused to contact with at least one absorbing agent selected from silica gels, molecular sieves, activated carbon, iron particles, copper particles and zinc particles or an alkali aqueous solution, thereby removing reaction by-products.

[8] A quantitative analysis method for a gas component contained in a halogen fluoride mixed gas, characterized by reacting a mixed gas containing a halogen fluoride containing bromine or iodine and another gas component with a removing agent, thereby removing the halogen fluoride in the mixed gas, further removing produced by-products, and quantitatively analyzing a residual gas by a gas chromatograph, wherein the removing agent is a chloride, bromide or iodide of an element selected from the group consisting of potassium, sodium, magnesium, calcium and barium. [9] A quantitative analyzer for a gas component contained in a halogen fluoride mixed gas, comprising: a sample container filled with a mixed gas containing a halogen fluoride containing bromine or iodine and another gas component; a halogen fluoride removing tank; a by-product removing tank; and a gas chromatograph, wherein a removing agent is filled in the halogen fluoride removing tank, and a residual gas obtained by removing the halogen fluoride and the by-products from a sample gas is introduced into the gas chromatograph.

Advantageous Effects of Invention

According to the method for removing a halogen fluoride in the present invention, it is possible to efficiently remove the halogen fluoride containing bromine or iodine in a state in which the possibility of blocking of a pipe by a reactant is reduced. Therefore, it becomes possible to provide a method for removing in which the handling of an exhaust gas is facilitated.

Further, according to the quantitative analysis method and the quantitative analyzer in the present invention, it is possible to precisely quantify impurity components such as oxygen, nitrogen, carbon dioxide and tetrafluoromethane accompanying the halogen fluoride, which have not been conventionally known. Due to this, a high-purity halogen fluoride, which is used as an etching gas, etc. for a semiconductor, can be stably supplied.

BRIEF DESCRIPTION OF DRAWINGS

FIG. 1 is a schematic drawing showing an analyzer for performing evaluation in Examples 1 and 2.

FIG. 2 is a schematic drawing showing an analyzer for performing evaluation in Examples 3 to 10.

FIG. 3 is a schematic drawing showing an analyzer for performing evaluation in Examples 11 to 19.

DESCRIPTION OF EMBODIMENTS

Hereinafter, the method for removing the halogen fluoride from the mixed gas (hereinafter referred to as "halogen fluoride mixed gas" or "mixed gas" in some cases) containing the halogen fluoride containing bromine or iodine and another gas component, as well as the quantitative analysis method and the quantitative analyzer for the halogen fluoride in the mixed gas will be explained in detail.

As the halogen fluoride containing bromine or iodine, one or at least two selected from BrF, $BrF_3$, $BrF_5$, $IF_3$, $IF_5$ and $IF_7$ is/are used.

Another gas component contained in the mixed gas includes impurity components and diluent gas, etc.

The impurity components include gases such as oxygen, nitrogen, carbon dioxide and tetrafluoromethane, etc.; as well as volatile metal fluorides such as silicon tetrafluoride, sulfur hexafluoride, tungsten hexafluoride and chromium pentafluoride, etc. Many of them originate from halogen fluoride production. Further, the above diluent gas components include inert gases such as nitrogen, helium and argon, etc. and they are mixed in from the viewpoint of safety and corrosion, etc.

The content of another gas component in the mixed gas may be generally an impurity gas quantity of about 1 volppm to 5 vol % with respect to the halogen fluoride or may be generally a diluent gas quantity of about 10 to 90 vol %. Meanwhile, the above content may be a quantity outside these ranges and is not particularly limited.

The mixed gas may contain only one of another gas component and may also contain two or more of them. If two or more of the other gas components are included, their content is not particularly limited. Two or more kinds of trace quantities of other gas components may be contained, two or more kinds of large quantities of other gas components may be contained, or a trace quantity of another gas component and a large quantity of another gas component may be contained in a mixed state.

In accordance with the method for removing in the present invention, the halogen fluoride in the mixed gas is removed.

The quantitative analysis method in the present invention can analyze not only trace components alone, or a large quantity of components alone, but can also quantitatively analyze a component in which the trace components and a large quantity of components are mixed.

According to the present invention, first, the mixed gas containing the halogen fluoride and another gas component is made to react with a removing agent, thereby removing the halogen fluoride and also removing the produced by-products.

As the removing agent, a metal chloride, metal bromide and metal iodide can be used.

During the reaction with the removing agent, the halogen portion (excluding fluorine) and the fluorine portion in the halogen fluoride are separated, and the fluorine portion reacts with metal salt of the removing agent to become metal salt fluoride, so that chlorine, bromine and iodine are generated to be recovered. As for the quantity of the removing agent, the removing agent could be contained in an excessive quantity equal to or larger than the reaction equivalent with respect to the halogen fluoride. Further, in case of performing a successive treatment, the quantity of the removing agent could be an excessive quantity with respect to a circulation quantity, for example, 3 to 30 times the reaction equivalent, preferably, 5 to 10 times the reaction equivalent.

As the metal chloride, a potassium chloride, sodium chloride, magnesium chloride, calcium chloride or barium chloride is suitable, because it is available as a comparatively high-purity and inexpensive reagent. As the metal bromide, a potassium bromide, sodium bromide, magnesium bromide, calcium bromide or barium bromide is suitable, because it is available as a comparatively high-purity and inexpensive reagent. As the metal iodide, a potassium iodide, sodium iodide, magnesium iodide, calcium iodide or barium iodide is suitable, because it is available as a comparatively high-purity and inexpensive reagent.

For example, when potassium chloride is used as the removing agent and is made to react with bromine pentafluoride, due to the chemical reaction of Formula (1) indicated below, potassium fluoride, bromine and chlorine are generated.

$$10KCl + 2BrF_5 \rightarrow 10KF + Br_2 + 5Cl_2 \quad (1)$$

When potassium bromide is used as the removing agent and is made to react with bromine pentafluoride, due to the chemical reaction of Formula (2) indicated below, potassium fluoride and bromine are generated.

$$5KBr + BrF_5 \rightarrow 5KF + 3Br_2 \quad (2)$$

When potassium iodide is used as the removing agent and is made to react with iodine heptafluoride, due to the chemical reaction of Formula (3) indicated below, potassium fluoride and iodine are generated.

$$7KI + IF_7 \rightarrow 7KF + 4I_2 \quad (3)$$

The reaction of the halogen fluoride with the removing agent can be performed at, for example, 10° C. or higher to lower than 300° C., and the reaction also proceeds comparatively easily at approximately room temperature. Meanwhile, in order to increase the reaction speed and completely terminate the substitution reaction, the reaction temperature is preferably 100° C. or higher and more preferably 150° C. or higher when the removing agent is bromide or iodide. Further, if the removing agent is chloride, the reaction temperature is preferably 10° C. or higher to lower than 100° C., more preferably 15° C. or higher to 95° C. or lower and still more preferably 20° C. or higher to 90° C. or lower. If the temperature is increased too much, it could corrode pipes. The method according to the present invention would rarely cause the pipe blockage due to substance transfer by a reaction product.

The above reaction is carried out in a normal gas phase. When the mixed gas containing the halogen fluoride and another gas component is made to pass through a reaction pipe filled with the removing agent and to react with the removing agent therein, the metal fluoride deposits and remains inside the reaction pipe, so that another gas component and by-product halogen molecules are emitted from the reaction pipe, and hence another gas component in the mixed gas does not substantially react with the removing agent.

The above by-products such as chlorine, bromine and iodine are adsorbed or absorbed to be removed by making the reaction product contact with an adsorbing agent or absorbing agent. For example, adsorbing agents such as silica gels, molecular sieves and activated carbon, reacting agents such as iron particles, copper particles and zinc particles or absorbing agents containing an alkali aqueous solution can be used. The alkali aqueous solution indicates one having a pH value of about 9 to 14, but is not particularly limited thereto.

According to the method for removing in the present invention, the comparatively stable gases such as tetrafluoromethane and sulfur hexafluoride in another gas component (residual gas) which is neither adsorbed nor absorbed are adsorbed by the adsorbing agent such as activated carbon and zeolite, while the gas components having comparatively high reactivity such as a silicon tetrafluoride, tungsten hexafluoride and chromium pentafluoride are separated by being dissolved by soda lime, etc. The inert gases such as nitrogen and argon as the residual impurity components can be reused as a diluent gas or be emitted into the atmosphere.

Meanwhile, according to the quantitative analysis method in the present invention, the quantitative analysis is conducted by a gas chromatograph on another gas component (residual gas) which is neither adsorbed nor absorbed, and thereby another gas component contained in the mixed gas is capable of being quantitatively analyzed based on weight variations before and after the reaction as well as the result of the quantitative analysis in the residual gas.

A filler for a gas chromatographic column can be optionally selected based on another gas component as targeted, and molecular sieves 13X are preferable in case of quantitatively analyzing oxygen and nitrogen. Further, a detector for the gas chromatograph can also be optionally selected, while a thermal conductivity detector (TCD) is preferable from the viewpoint of practicality.

Next, a further concrete explanation will be made by using FIG. 1 showing an apparatus used for the analysis method according to the present invention.

The analyzer according to the present invention comprises a sample gas cylinder 1 filled with a mixed gas containing halogen fluoride and another gas component, a cylinder 2 filled with a diluent gas, pipes connected to these containers and air supplying mechanisms 3 for these pipes, a halogen fluoride removing tank 4, a by-product removing tank 5 and a gas chromatograph 7. The analyzer also comprises a flow path switching valve 6 and a scrubbing tank 8 for emission, if necessary. The halogen fluoride removing tank is filled with a removing agent and, at the same time, a (non-illustrated) heating means is provided if necessary, while the by-product removing tank is filled with the above-mentioned adsorbing/absorbing agent. The diluent gas is mixed with a sample gas, while it can also be used as a carrier gas for the measurement using the gas chromatograph. In FIG. 1, the diluent gas from the same cylinder 2 is mixed with the sample gas, while the carrier gas may be supplied from another cylinder. As the carrier gas, the inert gases such as a nitrogen gas, helium and argon, as well as a hydrogen gas can be used.

The mixed gas is sent together with the diluent gas to the halogen fluoride removing tank 4 through the air supplying mechanism 3 by, for example, a mass flow controller (MFC), so that the mixed gas is reacted with the removing agent and the by-products after the reaction is removed in the by-product removing tank 5. Then, the remaining gas is mixed with the diluent gas if necessary and passes through, as the sample gas, a sample measuring pipe and a flowmeter to be quantitatively analyzed in the gas chromatograph 7. While the sample gas is exhausted after the quantitative analysis, an exhaust gas can also be exhausted after having impurities removed, if necessary, through the scrubbing tank 8 filled with an adsorbing agent such as activated carbon and zeolite or a decomposing agent such as soda lime.

The sample gas having been introduced into the gas chromatograph is separated in the column filled with a filler for the gas chromatograph, and detected by the thermal conductivity detector. A peak area of a standard gas analyzed beforehand in accordance with the same operation is compared with a peak area of a trace component of the sample gas, so that the concentration of the trace component can be known.

EXAMPLES

The invention according to the present embodiment will be concretely explained further hereinafter in accordance with examples, while the invention according to the present embodiment is not limited to only the examples described below.

Example 1

A gas composition containing bromine pentafluoride was analyzed as a sample gas in accordance with the quantitative analysis method according to the present invention. The analysis was conducted by means of an analyzer shown in FIG. 1.

The halogen fluoride removing tank 4 filled with potassium bromide as the removing agent was used, an adsorbing pipe filled with silica gels was used as the by-product removing tank 5, and a column filled with the molecular sieves 13X was used as the gas chromatograph 7. The reaction of the sample gas and the potassium bromide was set to 200° C. Further, helium was used as the carrier gas.

According to the analysis result using the gas chromatograph, the sample gas contained at most 240 volppm of $N_2$ and 5 volppm of $O_2$ and the remainder was composed of bromine pentafluoride. When a column inlet and the detector of the gas chromatograph were checked, no corrosion due to the bromine pentafluoride was seen.

Example 2

A gas composition containing iodine heptafluoride was analyzed as a sample gas in accordance with the quantitative analysis method according to the present invention. The analysis was conducted by means of the analyzer shown in FIG. 1.

The halogen fluoride removing tank 4 filled with potassium iodide as the removing agent was used, an adsorbing pipe filled with silica gels was used as the by-product removing tank 5, and a column filled with the molecular sieves 13X was used as the gas chromatograph 7. The reaction of the sample gas and the potassium iodide was set to 200° C. Further, helium was used as the carrier gas.

According to the analysis result using the gas chromatograph, the sample gas was composed of at most 320 volppm of $N_2$ and 5 volppm of $O_2$, and the remainder was composed of iodine heptafluoride. When a column inlet and the detector of the gas chromatograph were checked, no corrosion due to the iodine heptafluoride was recognized.

Comparative Example 1

Except for using a reaction pipe filled with $Ca(OH)_2$ in place of the removing agent, the analysis was conducted with the same method as in Example 1. The temperature of the reaction pipe was set to 200° C.

As a result of the reaction of the bromine pentafluoride and $Ca(OH)_2$, a large quantity of $O_2$ was detected and therefore $O_2$ and $N_2$ were not separated, so that $N_2$ could not be quantified.

Example 3

As shown in FIG. 2, a cylindrical halogen fluoride removing tank 4 having an inner diameter of 50.8 mm and a length of 900 mm was filled with calcium chloride (produced by Tokuyama; 2560 g) having a particle size of 3 to 20 mm. The bromine pentafluoride from the sample gas cylinder 1 (sample container) was diluted from the diluent gas cylinder 2 to have a concentration of 10 vol % by nitrogen, and the thus diluted gas was distributed into the halogen fluoride removing tank 4 under conditions of an empty cylinder reference linear velocity of 0.6 m/min, 25° C. and atmospheric pressure. An infrared spectral analyzer (FT-IR) 9 was connected to an emission port of the halogen fluoride removing tank 4, the bromine pentafluoride gas concentration of a fluid exiting from the halogen fluoride removing tank 4 was measured, and the distribution of the bromine pentafluoride was stopped when the concentration exceeded 1 ppm, so as to determine the quantity of processing of the bromine pentafluoride having been processed until the distribution was stopped. As a result, bromine pentafluoride of 201 g could be removed as shown in Table 1 and no rapid heat generation nor no blockage in pipes, etc. were present at that time.

Example 4

Except for using potassium chloride (produced by Kanto Chemical) in place of the calcium chloride and setting the temperature of the halogen fluoride removing tank 4 to 90° C., the bromine pentafluoride was processed in accordance with the same method as in Example 3. The results are shown in Table 1. No blockage in pipes, etc. was confirmed.

Example 5

Except for using magnesium chloride (produced by Kanto Chemical) in place of the calcium chloride, the bromine pentafluoride was processed in accordance with the same method as in Example 3. The processing results are shown in Table 1. No blockage in pipes, etc. was confirmed.

Example 6

Except for setting the concentration of the distributed bromine pentafluoride to 1 vol %, the bromine pentafluoride was processed in accordance with the same method as in Example 3. The processing results are shown in Table 1. No blockage in pipes, etc. was confirmed.

Example 7

Except for setting the concentration of the distributed bromine pentafluoride to 20 vol %, the bromine pentafluoride was processed in accordance with the same method as in Example 3. The processing results are shown in Table 1. No blockage in pipes, etc. was confirmed.

Example 8

Except for using iodine heptafluoride as a processing gas, measuring the iodine heptafluoride gas concentration of the fluid exiting from the halogen fluoride removing tank 4, and stopping the distribution of the iodine heptafluoride when the concentration exceeded 1 ppm, the iodine heptafluoride was processed in accordance with the same method as in Example 3. The processing results are shown in Table 1. No blockage in pipes, etc. was confirmed.

Example 9

Except for using potassium iodide (produced by Kanto Chemical) in place of the calcium chloride and setting the temperature of the halogen fluoride removing tank 4 to 100° C., the bromine pentafluoride was processed in accordance with the same method as in Example 3. The processing results are shown in Table 1. No blockage in pipes, etc. was confirmed.

Example 10

Except for using iodine heptafluoride as the processing gas, using potassium iodide (produced by Kanto Chemical) in place of calcium chloride, setting the temperature in the halogen fluoride removing tank 4 to 100° C., measuring the iodine heptafluoride gas concentration of the fluid exiting from the halogen fluoride removing tank 4, and stopping the distribution of the iodine heptafluoride when the concentration exceeded 1 ppm, the iodine heptafluoride was processed in accordance with the same method as in Example 3. The processing results are shown in Table 1. No blockage in pipes, etc. was confirmed.

Example 11

As shown in FIG. 3, the bromine pentafluoride was processed in accordance with the same method as in Example 3 except for: providing, at the exhaust port 9 of an infrared spectral analyzer 9, a cylindrical by-product removing tank 5 having an inner diameter of 76.2 mm and a length of 900 mm, filled with silica gels (produced by Kanto Chemical; 2038 g) having a particle size of 2 to 4 mm; connecting an ultraviolet-visible absorptiometer (UV-Vis) 10 to the emission port of the by-product removing tank 5; measuring the chlorine gas concentration of the fluid exiting from the by-product removing tank 5; and stopping the distribution of the bromine pentafluoride when the concentration exceeded 1 ppm. The processing results are shown in Table 1. No blockage in pipes, etc. was confirmed.

Example 12

Except for using the molecular sieves 13X (produced by Union Showa) in place of the silica gels, the bromine pentafluoride was processed in accordance with the same method as in Example 11. The processing results are shown in Table 1. No blockage in pipes, etc. was confirmed.

Example 13

Except for using the molecular sieves 5A (produced by Union Showa) in place of the silica gels, the bromine pentafluoride was processed in accordance with the same method as in Example 11. The processing results are shown in Table 1. No blockage in pipes, etc. was confirmed.

Example 14

Except for using activated carbons (granular SHI-RASAGI®; produced by Osaka Gas Chemicals) in place of the silica gels, the bromine pentafluoride was processed in accordance with the same method as in Example 11. The processing results are shown in Table 1. No blockage in pipes, etc. was confirmed.

Example 15

Except for using $Al_2O_3$ of 90 wt %-$Na_2O$ of 10 wt % (produced by BASF) in place of the silica gels, the bromine pentafluoride was processed in accordance with the same method as in Example 11. The processing results are shown in Table 1. No blockage in pipes, etc. was confirmed.

Example 16

Except for using granular Fe (produced by Kanto Chemical) in place of the silica gels, the bromine pentafluoride was processed in accordance with the same method as in Example 11. The processing results are shown in Table 1. No blockage in pipes, etc. was confirmed.

Example 17

Except for using granular Cu (produced by Kanto Chemical) in place of the silica gels, the bromine pentafluoride was processed in accordance with the same method as in Example 11. The processing results are shown in Table 1. No blockage in pipes, etc. was confirmed.

Example 18

Except for using granular Zn (produced by Kanto Chemical) in place of the silica gels, the bromine pentafluoride was processed in accordance with the same method as in Example 11. The processing results are shown in Table 1. No blockage in pipes, etc. was confirmed.

Example 19

Except for setting the temperature in the halogen fluoride removing tank to 150° C., the bromine pentafluoride was processed to be removed in accordance with the same method as in Example 3. As a result, approximately the same quantity of bromine pentafluoride as the one in Example 3 could be processed, while slight corrosion in pipes was confirmed.

Comparative Example 2

The bromine pentafluoride was processed to be removed in accordance with the same method as in Example 3 except for using, as the removing agent, in place of the calcium chloride, only soda lime (produced by Yabashi Industries; composed of calcium hydroxide $Ca(OH)_2$ (about 75 wt %), water $H_2O$ (about 20 wt %), sodium hydroxide NaOH (about 3 wt %) and potassium hydroxide KOH(about 1 wt %)). As a result, since the value of a pressure gauge installed at the inlet of the halogen fluoride removing tank increased during the reaction, it was determined that the halogen fluoride removing tank was blocked, and the distribution of the bromine pentafluoride was stopped. The quantity of the bromine pentafluoride having been processed until the stop of the distribution was 47 g. When the halogen fluoride removing tank was opened and its interior was observed, generation of brown slurry was recognized. The results are shown in Table 1.

TABLE 1

| | Processing gas (halogen fluoride) | Diluent gas | Removing agent in halogen fluoride removing tank (tank temperature) | Content in by-product removing tank (tank temperature) | Halogen fluoride removal quantity |
|---|---|---|---|---|---|
| Example 3 | $BrF_5$ 10 vol % | $N_2$ 90 vol % | $CaCl_2$ 25° C. | Not used | 230 g |
| Example 4 | $BrF_5$ 10 vol % | $N_2$ 90 vol % | KCl 90° C. | Not used | 87 g |
| Example 5 | $BrF_5$ 10 vol % | $N_2$ 90 vol % | $MgCl_2$ 25° C. | Not used | 152 g |
| Example 6 | $BrF_5$ 1 vol % | $N_2$ 99 vol % | $CaCl_2$ 25° C. | Not used | 262 g |
| Example 7 | $BrF_5$ 20 vol % | $N_2$ 80 vol % | $CaCl_2$ 25° C. | Not used | 179 g |
| Example 8 | $IF_7$ 10 vol % | $N_2$ 90 vol % | $CaCl_2$ 25° C. | Not used | 171 g |
| Example 9 | $BrF_5$ 10 vol % | $N_2$ 90 vol % | KBr 100° C. | Not used | 183 g |
| Example 10 | $IF_7$ 10 vol % | $N_2$ 90 vol % | KI 100° C. | Not used | 157 g |
| Example 11 | $BrF_5$ 10 vol % | $N_2$ 90 vol % | $CaCl_2$ 25° C. | Silica gels 25° C. | 202 g |
| Example 12 | $BrF_5$ 10 vol % | $N_2$ 90 vol % | $CaCl_2$ 25° C. | Molecular sieves 13X 25° C. | 215 g |
| Example 13 | $BrF_5$ 10 vol % | $N_2$ 90 vol % | $CaCl_2$ 25° C. | Molecular sieves 5A 25° C. | 202 g |
| Example 14 | $BrF_5$ 10 vol % | $N_2$ 90 vol % | $CaCl_2$ 25° C. | Activated carbon 25° C. | 208 g |
| Example 15 | $BrF_5$ 10 vol % | $N_2$ 90 vol % | $CaCl_2$ 25° C. | $Al_2O_3$ of 90 wt %-$Na_2O$ of 10 wt % 25° C. | 136 g |
| Example 16 | $BrF_5$ 10 vol % | $N_2$ 90 vol % | $CaCl_2$ 25° C. | Fe particles 25° C. | 78 g |
| Example 17 | $BrF_5$ 10 vol % | $N_2$ 90 vol % | $CaCl_2$ 25° C. | Cu particles 25° C. | 96 g |
| Example 18 | $BrF_5$ 10 vol % | $N_2$ 90 vol % | $CaCl_2$ 25° C. | Zn particles 25° C. | 124 g |
| Example 19 | $BrF_5$ 10 vol % | $N_2$ 90 vol % | $CaCl_2$ 150° C. | Not used | 220 g |
| Comparative Example 2 | $BrF_5$ 10 vol % | $N_2$ 90 vol % | Soda lime 25° C. | Not used | 47 g |

INDUSTRIAL APPLICABILITY

It is possible to provide a method for removal in which a halogen fluoride containing bromine or iodine in a mixed gas can be easily separated. Due to this, a gas used in semiconductor processing can be subjected to exhaust gas treatment safely, with high treatment efficiency and continuously during a long period.

Moreover, according to the present invention, it is possible to provide a quantitative analysis method for trace impurities in a halogen fluoride. This allows a high-purity halogen fluoride to be stably supplied.

REFERENCE SIGNS LIST

1: Sample gas cylinder
2: Diluent gas cylinder
3: Air supplying mechanism
4: Halogen fluoride removing tank
5: By-product removing tank
6: Flow path switching valve
7: Gas chromatograph
8: Scrubbing tank
9: Infrared spectral analyzer (FT-IR)
10: Ultraviolet-visible absorptiometer (UV-Vis)

The invention claimed is:

1. A method for removing a halogen fluoride in a mixed gas, characterized by reacting a mixed gas containing the halogen fluoride including bromine or iodine and another gas component with a removing agent which is a chloride, bromide or iodide of an element selected from the group consisting of potassium, sodium, magnesium, calcium or barium.

2. The method for removing a halogen fluoride according to claim 1, wherein a reaction temperature with the removing agent is 10° C. or higher and lower than 300° C.

3. The method for removing a halogen fluoride according to claim 1, wherein the halogen fluoride is at least one selected from BrF, $BrF_3$, $BrF_5$, $IF_3$, $IF_5$ and $IF_7$.

4. The method for removing a halogen fluoride according to claim 1, wherein the removing agent is a chloride of an element selected from the group consisting of potassium, sodium, magnesium, calcium and barium, and a reaction temperature of the mixed gas and the chloride is 10° C. or higher and lower than 100° C.

5. The method for removing a halogen fluoride according to claim 1, wherein the removing agent is a bromide or iodide of an element selected from the group consisting of potassium, sodium, magnesium, calcium and barium and a reaction temperature of the mixed gas and the bromide or iodide is 100° C. or higher and lower than 300° C.

6. The method for removing a halogen fluoride according to claim 1, wherein another gas component contains at least one selected from oxygen, nitrogen, carbon dioxide, helium, argon, tetrafluoromethane, silicon tetrafluoride, sulfur hexafluoride, tungsten hexafluoride and chromium pentafluoride.

7. The method for removing a halogen fluoride according to claim 1, wherein a reaction product is caused to contact with at least one adsorbing agent selected from silica gels, molecular sieves, activated carbon, iron particles, copper particles and zinc particles, or an alkali aqueous solution, thereby removing reaction by-products.

8. A quantitative analysis method for a gas component contained in a halogen fluoride mixed gas, characterized by reacting a mixed gas containing a halogen fluoride including bromine or iodine and another gas component with a removing agent, thereby removing the halogen fluoride in the mixed gas, further removing produced by-products and quantitatively analyzing a residual gas by a gas chromatograph, wherein the removing agent is a chloride, bromide or iodide of an element selected from the group consisting of potassium, sodium, magnesium, calcium and barium.

* * * * *